United States Patent [19]

Morita

[11] Patent Number: 4,907,036

[45] Date of Patent: Mar. 6, 1990

[54] DENSITOMETER FOR PHOTOGRAPHY

[76] Inventor: Minoru Morita, 33-7, Takashimadaira 2-chome, Itabashi-ku, Tokyo, Japan

[21] Appl. No.: 189,979

[22] Filed: May 4, 1988

[30] Foreign Application Priority Data

May 6, 1987 [JP] Japan ................................. 62-110139
May 6, 1987 [JP] Japan ................................. 62-110140

[51] Int. Cl.⁴ ................................................ G01J 3/51
[52] U.S. Cl. ...................................... 356/404; 356/73; 356/406; 356/418
[58] Field of Search ............... 356/404, 406, 407, 416, 356/418, 419, 443, 444, 73; 364/526

[56] References Cited

U.S. PATENT DOCUMENTS 3,102,202  8/1963  Sweet ................................. 356/443
4,082,458  4/1978  Fukui et al. ........................... 356/73
4,645,350  2/1987  Weidmann et al. ................. 356/418

Primary Examiner—F. L. Evans
Attorney, Agent, or Firm—Koda & Androlia

[57] ABSTRACT

A densitometer for photography comprising a disk on which are disposed filters of three colors at predetermined circumferential spacing for measuring the transmission and reflection densities of negative and color reversal film and color print, and a visual sensitivity filter for measuring the reflection and transmission densities of monochromatic and monochromatic reversal film. Lamps and a light-receiving element are provided to enable measurment of the densities. The disks are rotatingly driven by a motor to bring seven filters into alignment with the light-receiving element. Density from the output of the light-receiving element is measured and compared to a reference density, and an exposure time correction factor is computed from the density differences and resulting color and density correction values. The correction values and factor are displayed and the data is externally output via an interface.

3 Claims, 18 Drawing Sheets

FIG.7(A)
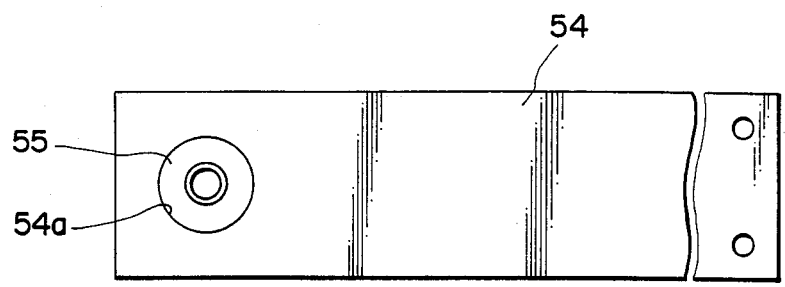
FIG.7(B)
FIG.8(A)    FIG.8(B)
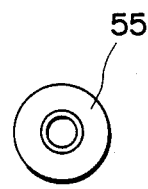   

DENSITOMETER FOR PHOTOGRAPHY

BACKGROUND OF THE INVENTION

The present invention relates to a densitometer for photography which is used for measuring the density of a photo such as a color print, a negative film and a reversal film, and for obtaining data such as exposure time correction data (so-called the slope correction) for color printer. The densitometer of the present invention also is applicable to the measurement of density in color printing.

FIGS. 1 to 4 illustrate conventional photographic densitometers.

A densitometer A shown in FIG. 1 has a transmission light receiving chamber 2 mounted to a specimen table 1 and an arm 3 which extends above the specimen table 1. To the arm 3 is mounted a cylinder 4, which is vertically movable. The transmission light receiving chamber 2 accommodates 12 light-transmitting receiving elements 5, three for each of four colors of red, green, blue and visual colors, as well as the same number of filters 6. An illuminating lamp 9 is disposed at the center of the space in the cylinder 4. A light diffusion plate 10 such as an opal glass fits in a sampling aperture 2a in the upper wall of the transmission light receiving chamber 2.

For the purpose of conducting measurement by the densitometer A, a specimen 11 is placed on the specimen table 1 and the cylinder 4 is lowered manually so as to bring the lower end of the cylinder 4 into close contact with the specimen 11. During measuring the reflection density, the light reflected by the upper surface of the specimen 11 is received by reflection light receiving elements 7 through the filters 8. During the measurement of the transmission density, the light which has been transmitted through the specimen 11 is diffused by a scattering diffusion plate 10 and is then received by the transmission light receiving element 5 through the filters 6.

A densitometer B shown in FIG. 2 has a lamp 13 for measurement of transmission density, which is disposed to a specimen table 12. At the same time, a disk 17 is mounted to an arm 15 in such a manner as to be rotated manually by means of a catch 18. At the same time, an optical-guide cylinder 19 is mounted in such a manner as to be manually movable up and down. At the same time, a light-receiving element 20 is fixed at a predetermined position.

The measurement with this densitometer B is conducted by manually rotating the disk 17 to bring a desired filter 16 into alignment with the light-receiving element 20, while lowering the optical guide cylinder 19, with the specimen placed on the specimen table 12. In operation, the light from the lamp 13 for transmission is passed through the specimen and an aperture 14 so as to be received by the light-receiving element 20 through the filter 16. This densitometer B is capable of measuring only the transmission density.

A densitometer C shown in FIG. 3 has an arm 23 which is vertically swingable with respect to a base plate 22. The arm 23 carries a disk 25 incorporating a plurality of filters 24, in such a manner that the disk 25 can be rotated manually by means of a catch 26. The densitometer C also has a light-receiving element 27, an optical guide cylinder 28 and a lamp 29 for reflection. The light from the reflection lamp 29 is projected from a focusing head 31 through an optical fiber 30.

The measurement with this densitometer C is effected by placing a specimen 32 under an aperture 21, and swinging the arm 23 downward so as to bring the focusing head 31 into alignment with the aperture 21, while manually rotating the disk 25 to bring the desired filter into alignment with the light-receiving element. The light from the lamp 29 for reflection is transmitted through the optical fiber 30 and is passed through the aperture 21 so as to impinge upon the specimen 32. The light reflected by the specimen 32 is received by the light-receiving element 27 via an aperture 31a of the focusing head 31 and the optical guide cylinder 28. This densitometer C is capable of measuring only the reflection density. The output from the light-receiving element 27 is transmitted from an output terminal 33 to the external data processing device and is processed by, for example, a CPU.

The densitometer D of FIG. 4 has, as is the case of the densitometer C shown in FIG. 3, an arm 36 which is vertically swingable with respect to the base plate 35 having a ring 35a. In this arrangement, the light from the lamp 37 for reflection is projected onto a focusing head 39 through an optical fiber 38. The reflected light incident to the aperture 39a of the focusing head 39 is received by four light-receiving elements 42 through four reflected light transmitting optical fibers 40 and then through the respective filters 41. This densitometer D can measure the reflection density by itself and can display the density value.

The conventional densitometers A to D described above have the following shortcomings:

(1) The mounting method and the mounting work for mounting the light-receiving element and the filters are generally complicated, with the result that the cost becomes high.

(2) It is not possible to obtain a uniform light.

(3) These densitometers are not capable of conducting measurement for reversal films.

(4) Wide installation area is required and the cost therefore is high because separate devices for measuring the reflection density and transmission density must be placed.

(5) The machines are operated manually and thus operation thereof requires the special skill.

(6) It is not possible to automatically analyze the measured data.

(7) These densitometers are not designed for enabling data processing, display and external output for the purpose of management of development.

In view of the above-described shortcomings of the conventional machines, an object of the present invention is to make it possible to conduct, with a single densitometer having a single light-receiving element, all kinds of photographic density measurement such as measurement of the color negative film transmission density, color print reflection density, color reversal film transmission density, monochromatic film transmission density, monochromatic print reflection density and monochromatic reversal film transmission density, and also to enable the single densitometer to externally display and output development administration data by automatically analyzing and computing the measured data.

SUMMARY OF THE INVENTION

In order to achieve the above object, the densitometer according to the present invention comprises: a disk on which are disposed at a predetermined circumferential spacing filters of three colors for measuring the transmission density of a negative film, filters of three colors for measuring the reflection density of a color print and for measuring the transmission density of a color reversal film, and a visibility filter for measuring the reflection density of a monochromatic film, a reflection density of a monochromatic density and the transmission density of a monochromatic reversal film; a lamp for enabling the measurement of the reflection densities; a lamp for enabling the measurement of the transmission densities; a light-receiving element; a motor for rotatingly driving the disks so as to bring seven filters into alignment with the light receiving element in a one-by-one fashion; a density measuring portion for measuring the density from the output of the light-receiving element; a density difference computing means for determining the difference between the measured density and the reference density stored in the memory; a color-key correction value computing means for computing a color-key correction value from the difference; a density-key correction value for computing the density-key correction value in the same manner; an exposure time correction factor computing means for computing the exposure time correction factor from the color-key correction value; a display means for displaying the computed color-key correction value, density-key correction value and the exposure-time correction factor; and an interface for externally outputting the data concerning these values and factor.

The densitometer of the present invention has the following features:

Firstly, a reflection density measuring lamp, a transmission density measuring lamp and a single light-receiving element are disposed at predetermined positions.

Secondly, a tri-color filter for measuring the transmission density of a negative film, a tri-color filter for measuring the reflection density of a color print and for measuring the transmission density of a color reversal film, and a visibility filter for measuring the reflection density of a monochromatic film, a reflection density of a monochromatic density and the transmission density of a monochromatic density and the transmission density of a monochromatic reversal film are disposed on a disk at a predetermined spacing in the circumferential direction.

Thirdly, the disk is adapted to be rotated by a motor so as to bring the seven filters into alignment with the light-receiving element in a one-by-one fashion.

Fourthly, an aperture is formed in a transparent guide plate contacting a measuring object, the aperture being intended for limiting the light which is applied by the reflection density measuring lamp to the measuring object or the light which is applied by the transmission density measuring lamp to the filter opposing to the light-receiving element through the measuring object.

BRIEF DESCRIPTION OF THE DRAWINGS

FIGS. 7(A) and 7(B) are a plan view and a sectional view of a transparent guide plate incorporated in the densitometer of FIG. 5;

FIGS. 8(A) and 8(B) are a plan view and a sectional view of an aperture;

PREFERRED EMBODIMENT

An embodiment of the present invention will be described hereinbelow. The description will be first made to the mechanical and optical features of the embodiment.

Figure 1:
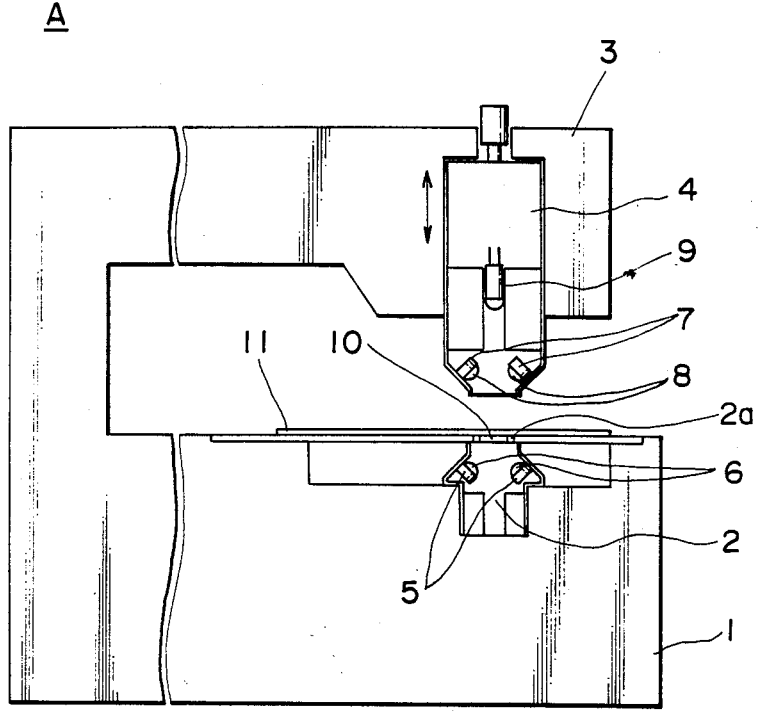
FIG. 1 is a sectional view of a conventional densitometer.
Figure 2:
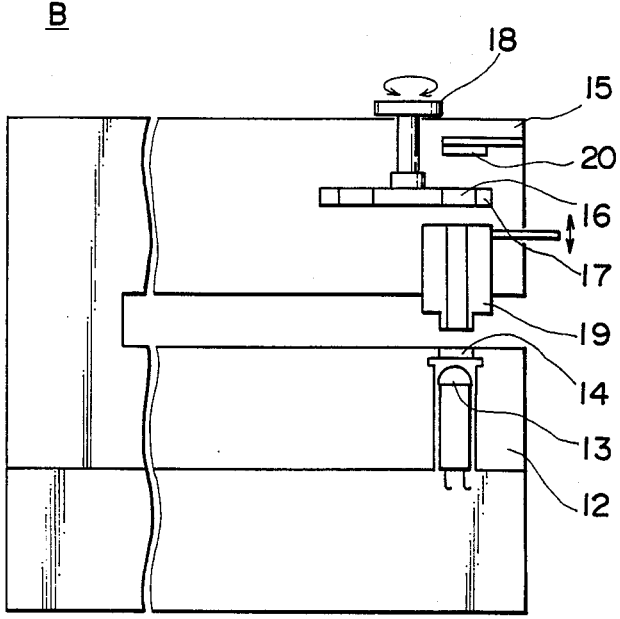
FIG. 2 is a sectional view of another conventional densitometer.
Figure 3:
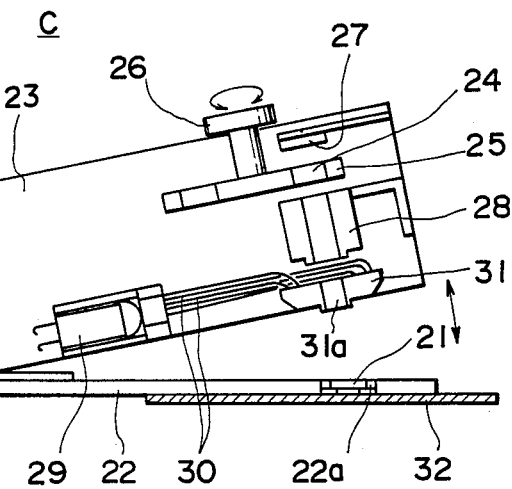
FIG. 3 is a sectional view of a further conventional densitometer.
Figure 4:
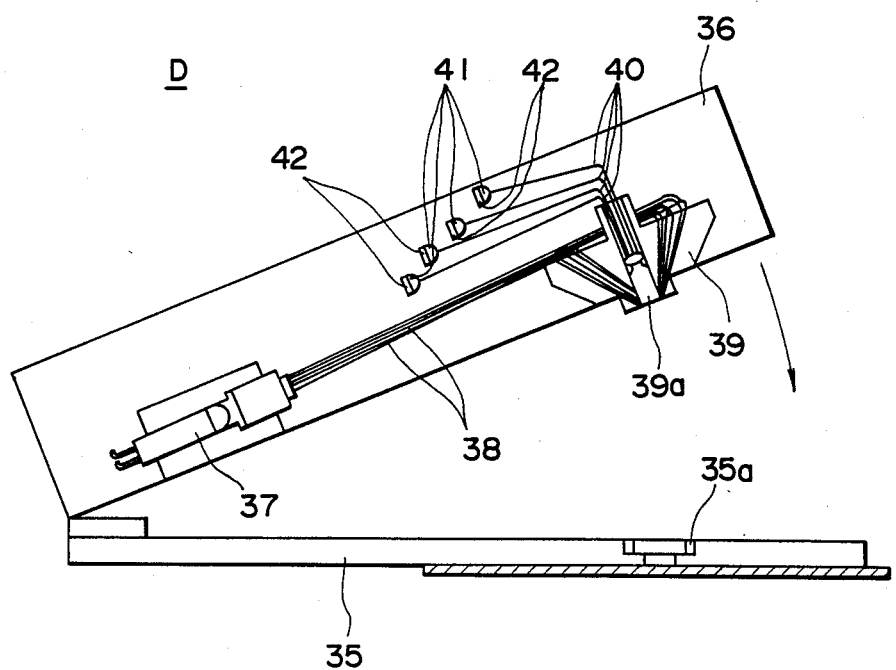
FIG. 4 is a sectional view of a still further conventional densitometer.
Figure 5:
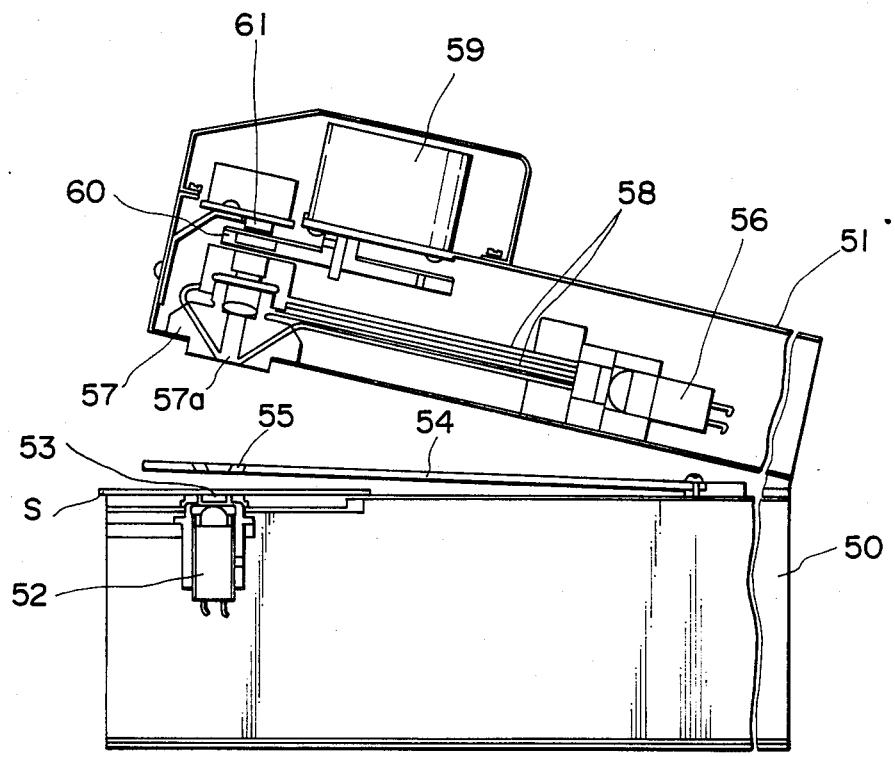
FIG. 5 is a sectional view of an embodiment of a densitometer according to the present invention.
Figure 6:
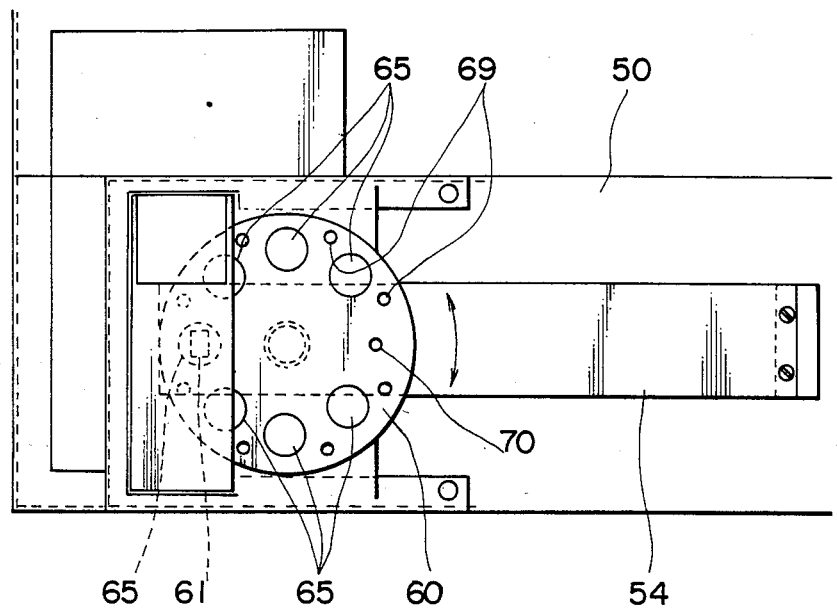
FIG. 6 is a plan view of the densitometer shown in FIG. 5.

Referring to FIG. 5 and 6, the densitometer has a hollow arm 51 which is swingably attached to the upper rear end of a specimen table 50. A lamp 52 for measuring the transmission density is disposed within the specimen table 50 at a level slightly below the top wall of the specimen table 50. The light from the lamp 52 is diffused and upwardly transmitted through a scattering diffusion plate 53 such as an opal glass fitted in the top wall of the specimen table 50.

A transparent guide plate 54 made of a transparent plastic material is secured at its rear end to the upper surface of the specimen table 50 in such a manner that it is positioned below the arm 51 and that it can be slightly swung up and down. As will be seen from FIGS. 7(A) and 7(B), the transparent guide plate 54 has an inverse frusto-conical aperture mounting hole 54a which receives an aperture 55 having an inverse frusto-conical shape as shown in FIGS. 8(A) and 8(B).

The arm 51 receives a lamp 56 for measuring the reflection density, a plurality of optical fibers through which the light from the lamp 56 is introduced to the end of the hole 57a of the focusing head 57, a motor 59, a disk 60 rotated by the motor 59, and a single light-receiving element 61. These parts are disposed at predetermined positions.

Figure 9:
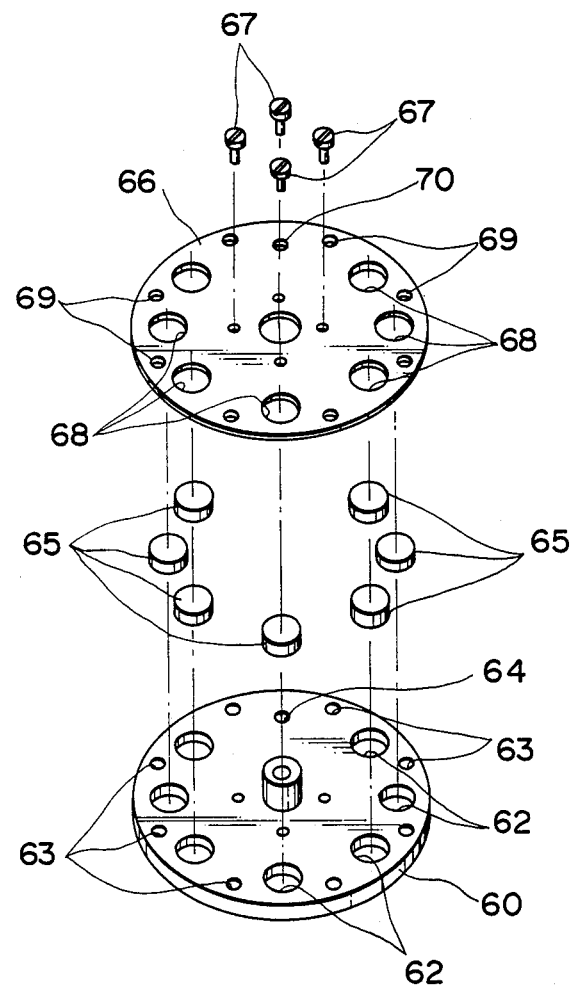
FIG. 9 is an exploded perspective view of a filter, a filter retainer plate and a disk.

As will be seen from FIG. 9, the disk 60 has seven filter holes 62 which are disposed at a predetermined circumferential spacing. The disk 60 also has eight stop position detection holes 63 corresponding to the filter holes and arranged at a predetermined circumferential spacing. The disk further has a single constant position detection hole 64 formed in a predetermined portion thereof. The disk 60 carries seven filters 65 including filters of three colors, i.e., red, green and blue, filters of three colors for measuring the reflection density of color print and transmission density of a color reversal film, and a single visual sensitivity filter for measuring the transmission density of monochromatic print and transmission density of monochromatic reversal film.

More specifically, these filters 65 are mounted in a manner which will be described hereinbelow.

Namely, the seven filters 65 are aligned with the corresponding filter holes 62 in the disk 60 and are pressed by a filter retainer plate 66. The filter retainer plate 66 is fixed to the disk 60 by means of a retainer screw 67. The filter retainer plate 66 is provided with seven filter holes 68, eight stop position detection holes 69 similar to those of the disk 60, and a single constant position detection hole 70. These holes in the filter retainer plate 66 correspond to the holes in the disk.

Figure 10:
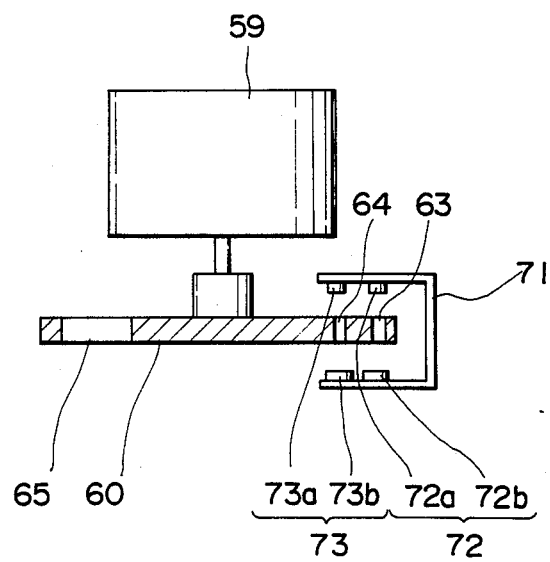
FIG. 10 is a front elevational view illustrating the relationship between the disk and the sensor.
Figure 11:
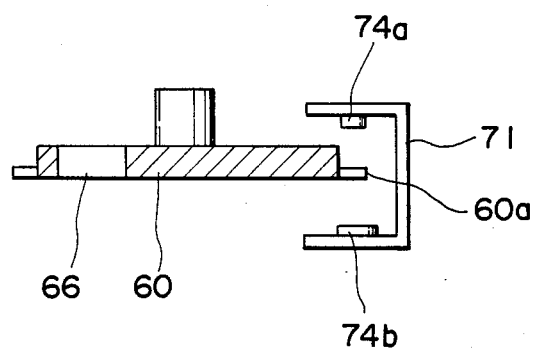
FIG. 11 is a front elevational view of another example of the relation between the disk and the sensor.

As will be seen from FIG. 10, any one of the eight stop position detection holes 63 can be brought to a position where it confronts a stop position detection sensor 72 which is composed of a light-emitting element 72a secured to a sensor base 71 and an opto-switch 72b, so as to be detected by the stop position sensor 72. Thus, the arrival of one of the seven filters 65 at the position where it confronts the light-receiving element 61 is detected by the stop position detection sensor 72.

Similarly, the constant position detection hole 64 is adapted to be detected by a constant position detection sensor 73 which is composed of a light-emitting element 73a secured to the sensor base 71 and an opto-switch 73b. Thus, the rotation of the disk 60 to a predetermined angular or rotational position is detected by means of the constant position detection sensor.

In the use of this densitometer, a specimen S to be measured is placed on the specimen table 50, and a transparent guide plate 54 is held in contact with the specimen S, as shown in FIG. 5. In this state, the disk 60 is rotated by the motor 59 so that a desired filter 65 is selected. For the purpose of measuring the transmission density, the lamp 52 for measuring the transmission density is turned on, and the light from the lamp 52 transmitted through the specimen S is received by the light-receiving element 61 via the aperture 55 and the hole 57a in the focusing head 57 and then through the selected filter 65.

For the purpose of measuring the reflection density, the lamp 56 for the measurement of the reflection density is turned on, and the light therefrom is applied to the specimen S through the optical fibers 58 and the end of the hole 57a of the focusing head 57 and then through the aperture 55. The light reflected by the specimen S is introduced into the aperture 55 and the hole 57a of the focusing head 57 so as to be received by the light-receiving element 61 through the filter 60.

Thus, according to the invention, it is possible to measure, by a single densitometer and with a single light-receiving element 61, various densities such as transmission density through the color negative film, reflection density from a color print, transmission density through a color reversal film, transmission density through a monochromatic film, reflection density from a monochromatic print, and transmission density through a monochromatic reversal film.

The detection of the stopping position and the constant position of the disk 60 is effected by means of a combination of a light-emitting element 74a secured to a sensor base 71 and an opto-switch 74b, which are arranged to detect a projection 60a provided on the disk 60. It is also possible to use a stepping motor 59 for rotating the disk 60, so that the sensors, holes and projection for detecting the rotational positions of the disk can be eliminated because the rotational position of the disk can be detected through an electrical control of the number of steps.

Figure 12:
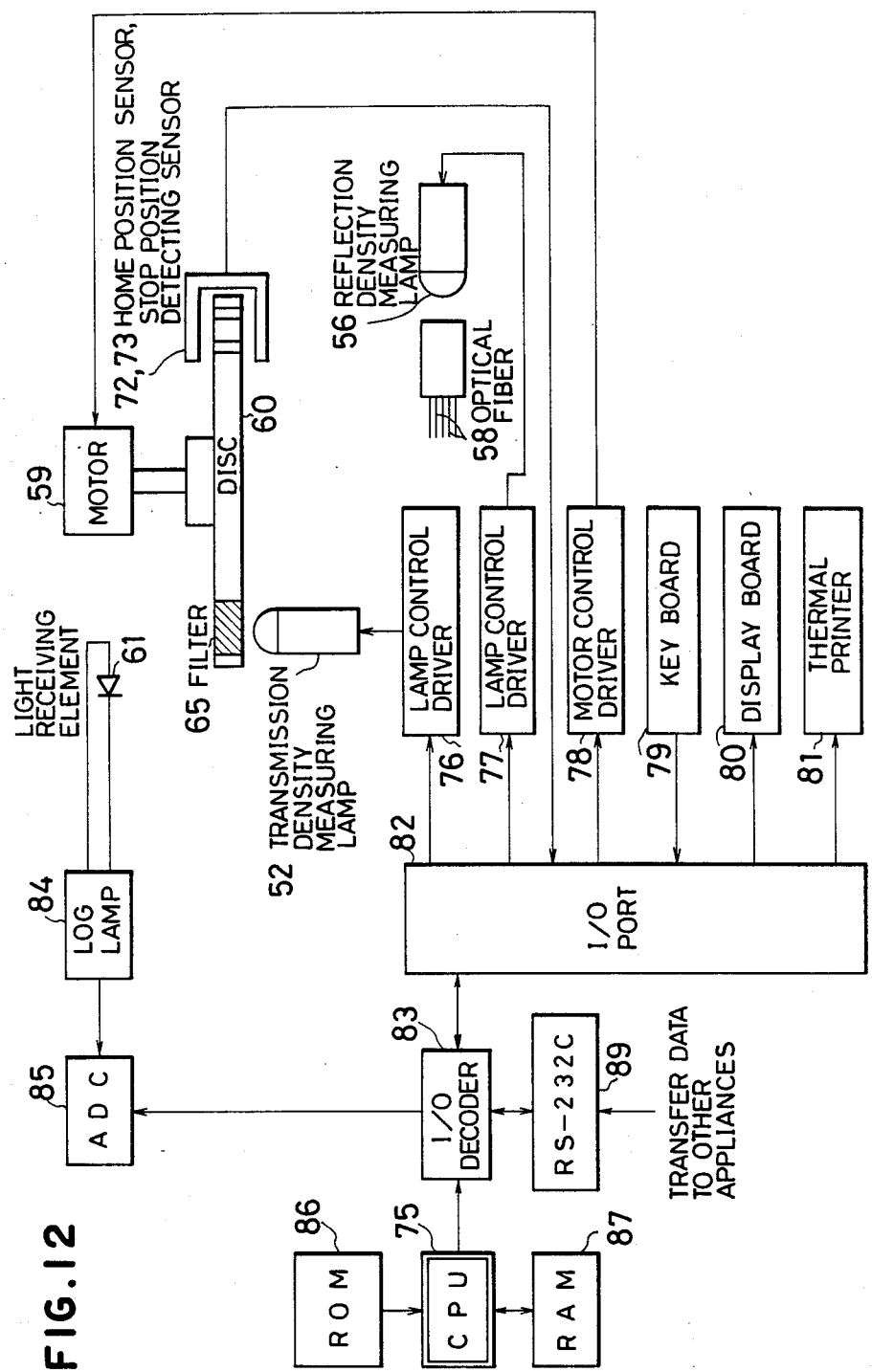
FIG. 12 is a block diagram of the electrical arrangement of the densitometer of the present invention.

A description will be made hereinunder as to the electrical arrangement. FIG. 12 is a block diagram of the electrical system. All kinds of operation are controlled by a CPU 75. In the description of this embodiment, the CPU 75 should be understood as including a computing processor.

The CPU 75 has an I/O port 82 to which are connected the stop position detection sensor 72, constant-position detection sensor 73, a lamp control driver 76 for turning on and off the lamp 52 for measuring the transmission density, a lamp control driver 77 for turning on and off the lamp 56 for measuring the reflection density, a motor control driver 78 for driving the motor 59, a keyboard 79, a display board 80 such as of liquid crystal type, and a printer 81 such as a thermal printer. Signals are exchanged between these devices and the CPU 75 through an I/O decoder 83. The analog output of the light-receiving element 61 is amplified by a LOG amplifier 84 and is converted into a digital signal by means of an analog-to-digital converter 85 and is further decoded by an I/O decoder 83 before delivered to the CPU 75.

Figure 13:
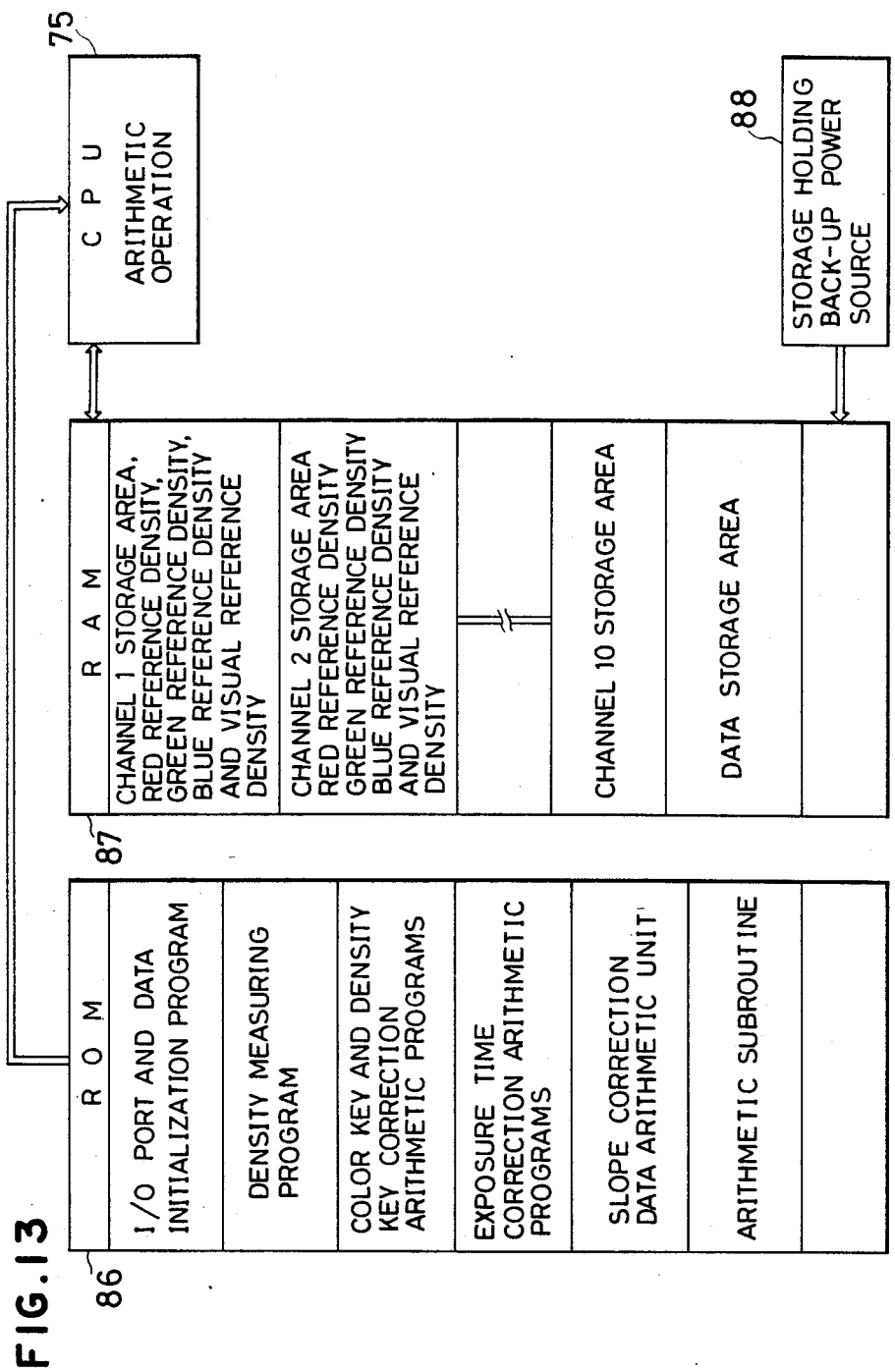
FIG. 13 is an illustration of a memory map.

As will be seen from FIG. 13, a ROM 86 stores a program for initializing the I/O port and the data, a density measuring program, a color-key and density-key correction computing program, exposure time correction computing program, slope correction data computing program, and computing sub-routines.

On the other hand, a RAM 87 provides storage areas such as channels 1 to 10 for later-mentioned computations, as well as areas for storing data. The recording areas of channels 1 to 10 store reference densities of three colors including red, green and blue, and the visual sensitivity reference density. The values to be stored are manually input through the keyboard 79 in accordance with the reference administration values appointed by the film manufacturer or by automatically measuring the paper or film for reference administration in the manner described above. The memory in the RAM 87 is held by a memory holding back-up power supply 88 and the computing data stored therein is output as desired to external devices via the I/O decoder 83 and through an interface such as an interface 89 specified as RS-232C.

Figure 14:
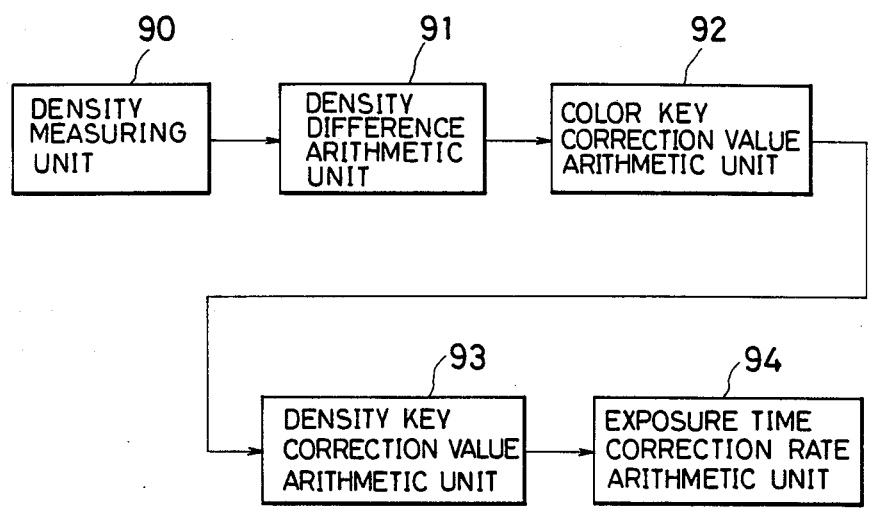
FIG. 14 is a block diagram illustrating a CPU sectioned according to functions.

From the viewpoint of functions, the CPU 75 used in this densitometer is composed of a density measuring portion 90, a density difference measuring portion 91, a color-key correction value computing portion 92, a density key correction value computing portion 94, as will be seen from FIG. 14. The operation of the CPU 75 will be described with reference to a flow chart.

Figure 15:
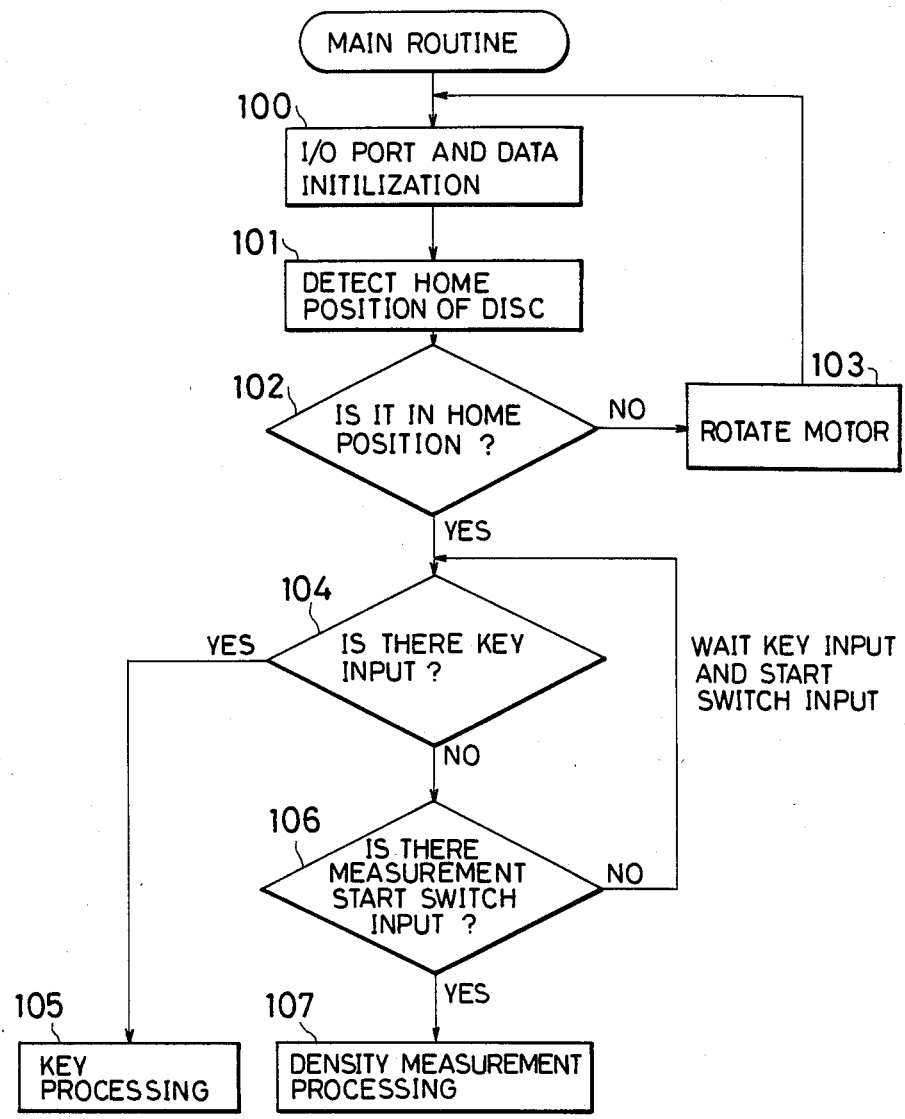
FIGS. 15, 16A, 16B, 17, 18A, 18B, 18C, 18D and 19 are flow charts of the process controlled by the CPU.

Referring to FIG. 15 which illustrates the main routine, the I/O port 82 and the data are initialized in Step 100. Then, constant position of the disk 60 is detected by the constant position detection sensor 73 in Steps 101 and 102. When the disk 60 is not in the constant position, i.e., when the constant position detection hole 70 is not detected by the constant position detection sensor 73, the motor 59 operates in Step 103 to rotate the disk 60. When the constant position is reached, a check is done in Step 104 for presence or absence of a key input from the keyboard 79. If there is any key input, a key process is executed in Step 105, whereas, when there is no key input, a judgement is done in Step 106 as to whether an input from a measurement start switch has been done. If the input has been received, the process proceeds to Step 107 for executing the density measuring process.

Figure 16A:
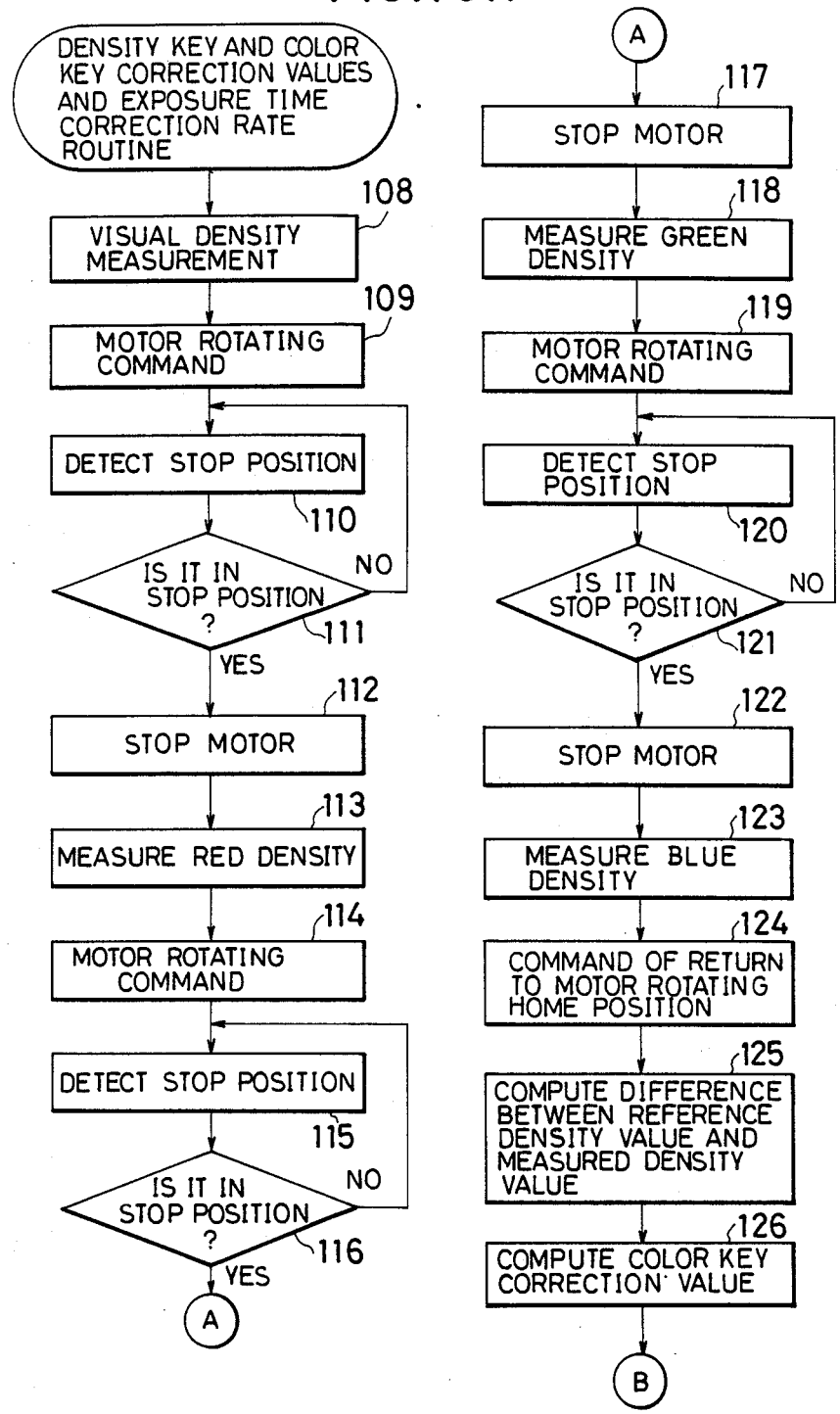
Figure 16B:
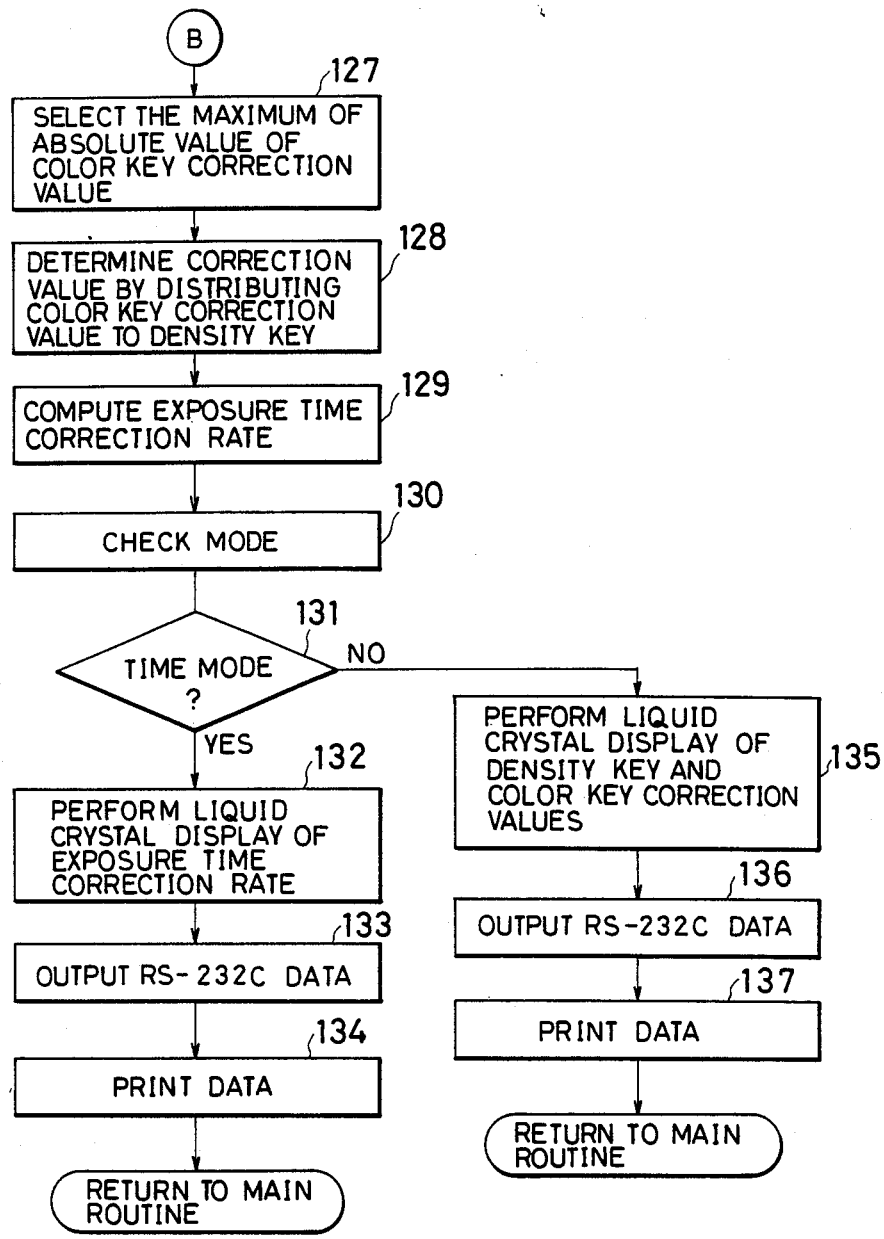

FIGS. 16A and 16B show a routine for computing the density-key and color-key correction values and the exposure time correction factor. This routine is commenced with Step 108 in which the visual density is measured by making use of a visual sensitivity filter 65. Then, process proceeds to Step 109 in which an instruction is given for driving the motor 59, Step 110 in which the stop position is detected, i.e., the stop position detection hole 63 in the disk 60 is effected by the stop position sensor 72, Step 111 in which a judgment is done as to whether the present position is a stop position, Step 112 in which the motor stops so as to select the red filter 66, and Step 113 in which measurement of red density is conducted. Subsequently, the green filter is selected in Step 118 in the same manner, i.e., through Step 114 in which an instruction is given to drive the motor 59, Step 115 in which the stop position is detected, Step 116 in which a judgment is done as to whether the instant position is a stop position, and Step 117 in which the motor is stopped. Then, the blue filter 65 is selected in Step 123 in the same manner, i.e., through Step 119 in which an instruction is given to drive the motor 59, Step 120 in which the stop position is detected, Step 121 in which a judgment is done as to whether the instant position is a stop position, and Step 122 in which the motor is stopped.

Then the process proceeds to Step 124 in which an instruction is given to drive the motor 59 and to reset the disk 60 to the constant position, whereby the disk 60 is detected by the constant position detection sensor 73. Then, the following computations are conducted while the disk 60 is reset in the constant position.

In Step 125, an operation is executed to compute the differences between the measured densities as measured in Steps 108, 113, 118 and 123 and the reference densities stored in the RAM 87, for each of the visual density, red density, green density and blue density.

In Step 126, an operation is conducted to determine the color-key correction by multiplying the difference values with the respective variable constants for each of the red, green and blue colors. The variable constants are determined in accordance with the difference in the visual density as obtained in Step 125.

In Step 127, an operation is done to compare the absolute values of the color-key correction as determined in Step 126, and the greatest one of the absolute values is selected.

In Step 128, the density-key correction value is determined by multiplying the greatest value determined in Step 127 with a density key correction factor which is a variable constant. In addition, correction values for the three colors are determined by subtracting the density-key correction value from the color-key corrections determined in Step 126.

In Step 129, the exposure time correction factors for three colors are determined by multiplying the color-key corrections of the three colors determined in Step 126 with the respective logarithmic variable constants.

Subsequently, a mode check operation is executed in Step 130 and a judgment is done in Step 131 as to whether the instant mode is a time mode. When the instant mode is the time mode, the process proceeds to Step 132 in which the exposure time correction factors for three colors as determined in Step 129 are displayed on the display board 80. At the same time, the data is output in Step 133 through the RS-232C interface and is printed by the thermal printer 81 in Step 134. The process then returns to the main routine shown in FIG. 5.

Figure 17:
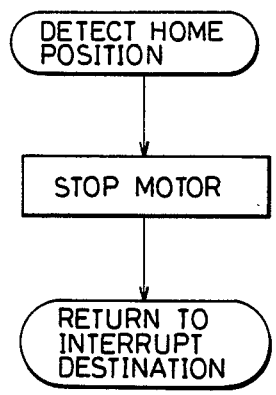
Figure 18A:
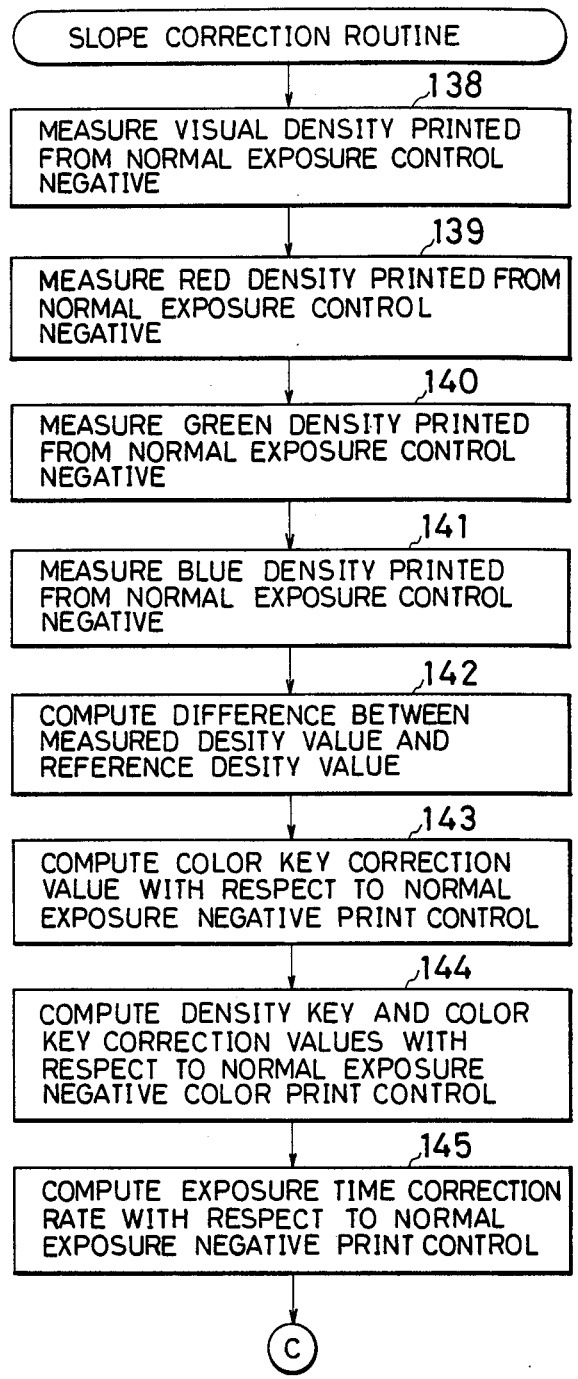
Figure 18B:
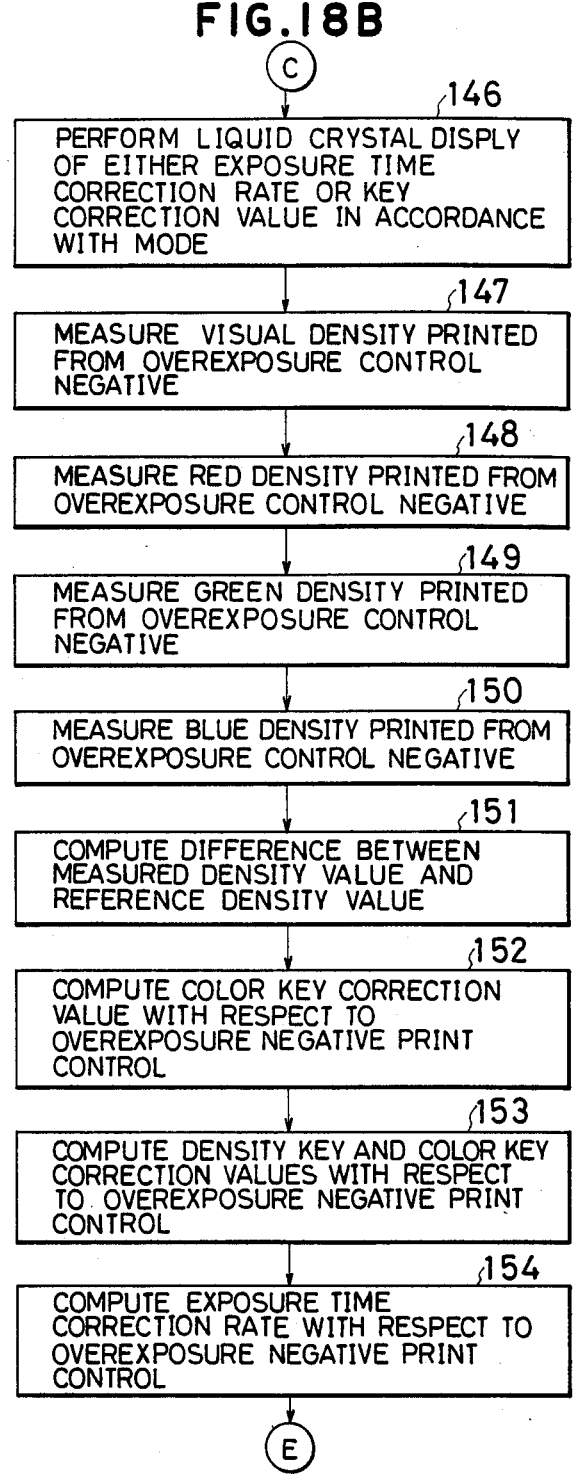
Figure 18C:
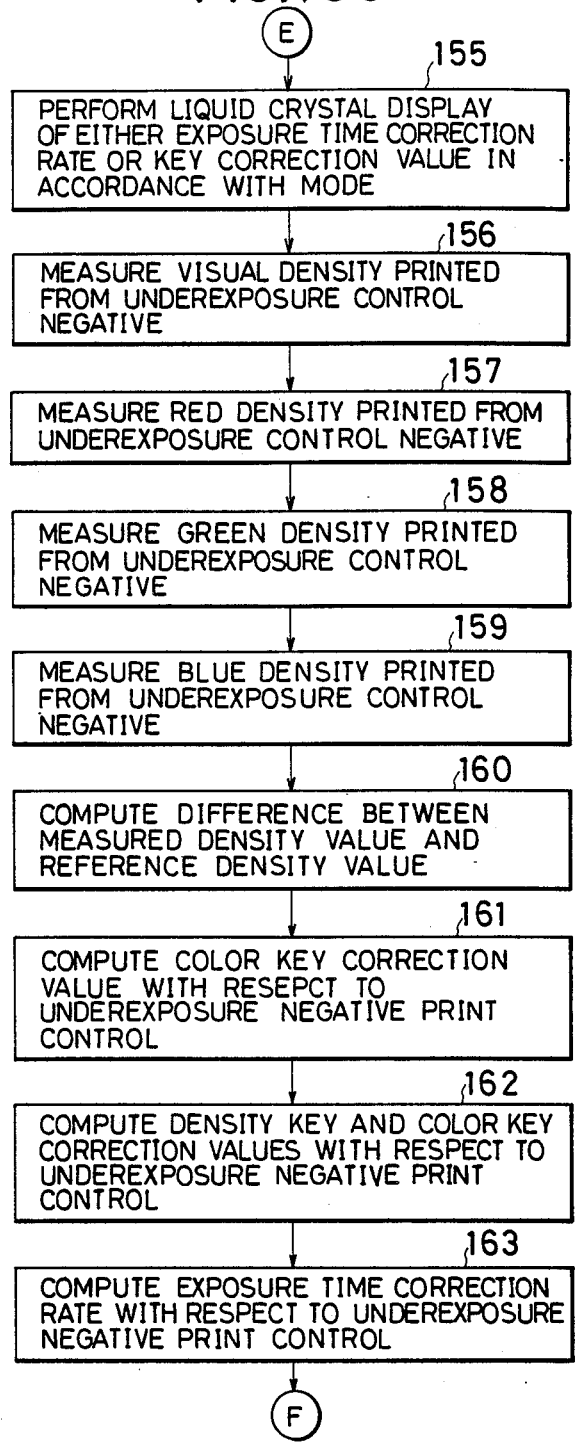
Figure 18D:
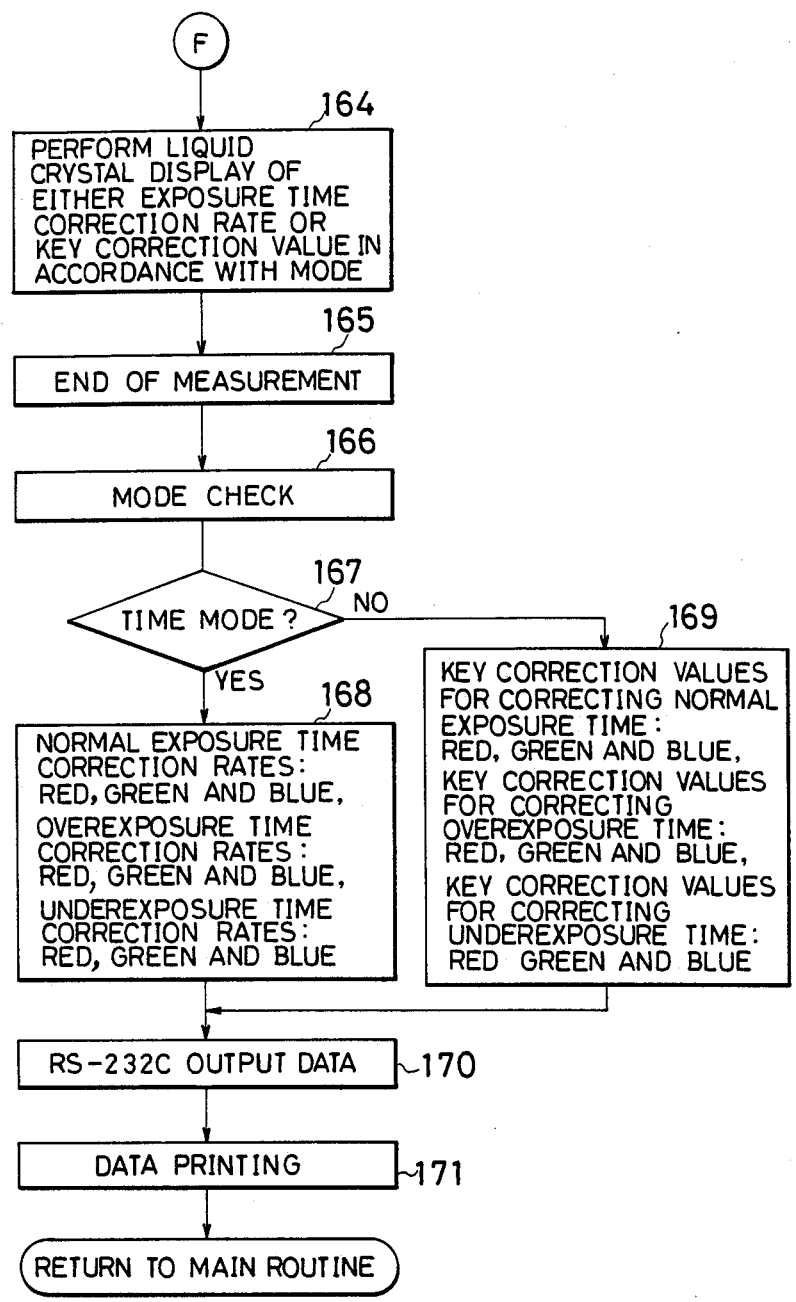

Conversely, when the instant mode is not the time mode, the process proceeds to Step 135 in which the density correction value determined in Step 128 and the color-key correction values for the three colors as determined in Step 128 are displayed on the liquid crystal display. Similarly, the data is output from the RS-232c interface 89 in Step 136. Then, printing is conducted in Step 137 by the thermal printer 81 and then returns to the main routine. When the detection of the constant position of the disk 60 is performed, an interruption is done to stop the motor 59 as shown in FIG. 17, and then the process is recovered.

As a result of the processing as shown in FIG. 16, the difference between three color density reference values and the measured three color density values are converted into the three color-key correction values and density key correction value for the color printer, and the exposure time correction value, and these values are displayed on the liquid crystal display and output externally.

A description will be made hereinbelow as to the slope correction routine as shown in FIGS. 18A, 18B, 18C and 18D. The term "slope correction" is used to mean an operation for setting up the exposure time of the color printer to enable the printing in AIM density from an administration negative film such as a normal negative film over-exposure negative film, under-exposure negative film, and so forth.

As is the case of the processing shown in FIGS. 16A and 16B, it is possible to sequentially conduct the measurement of the visual density printed from the exposure administration negative film (Step 138), measurement of the red density printed from the normal exposure administration negative film (Step 139), measurement of the green density printed from the normal exposure administration negative film (Step 140), and the measurement of the blue density printed from the normal exposure administration negative film (Step 141). Subsequently, in Step 142, the difference between the measured density and the reference density value is measured for each of the normal visual, normal red, normal green and normal blue, with the disk 60 set at the fixed position.

In the next step 143, the color-key correction is computed for each of the three colors with respect to the normal exposure negative print administration, by multiplying the difference of each of three color densities as determined in Step 142 with a variable constant.

In Step 144, the density key for the normal exposure negative print administration is computed by multiplying the greatest value of the three color corrections with a variable constant. In addition, the color key correction value for each of the three colors with respect to the normal exposure negative print administration is computed by subtracting the density key from the color key for each of the three colors.

In Step 145, the exposure time correction factors for the three colors are computed by multiplying color-key corrections for three colors determined in Step 143 with variable constants.

In Step 146, the exposure time correction factor or the key correction values are displayed on the liquid crystal display in accordance with the mode.

Then, steps are sequentially followed including Step 147 in which the visual density printed from the over exposure administration negative film is measured, Step 148 in which the red density from the over-exposure administration negative film is measured, Step 149 in which the green density from the over-exposure administration negative film is measured, and Step 150 in which the green density from the over-exposure administration negative film is measured. In Step 151, the difference between the measured density and the reference density is computed for each of the over-visual, over-red, over-green and over-blue.

In Step 152, the difference in density of each of three colors determined in Step 151 is multiplied with a variable constant so that the color-key correction for each of the three colors is computed for each of the over-exposure negative print administration.

In Step 153, the greatest value of the color-key correction for three colors as determined in Step 152 is multiplied with the variable constant so that the density key for the over-exposure negative print administration is computed. At the same time, the color-key correction values for the three colors are computed by subtracting the density keys from the color-key corrections of the three colors.

In Step 154, the color corrections of three colors as determined in Step 152 are multiplied with the variable constants so that the exposure time correction factors for the over-exposure negative print administration are computed for the three colors.

In Step 155, the exposure time correction factors or the key-correction values with respect to the over-exposure negative print are displayed on the liquid crystal display in accordance with the mode.

Subsequently, steps are sequentially followed including Step 156 in which the visual density printed from the under-exposure administration negative is measured, Step 157 in which the red density printed from the under-exposure administration negative is measured, Step 159 in which the green density printed from the under-exposure administration negative is measured, and Step 158 in which the green density printed from the under-exposure administration negative is measured. In Step 160, the difference between the measured density and the reference density is computed for each of the under-visual, under-red, under-green and under-blue.

In Step 161, the density difference of each of three colors as determined in Step 160 is multiplied with a variable constant so that the color-key correction is computed for each of the three colors.

In Step 162, the greatest value of the three color-key correction values as determined in Step 161 is multiplied with a variable constant, so that the density key with respect to the under-exposure negative print administration is computed. At the same time, the density keys are subtracted from the color corretions of the three colors so that the color-key correction values for the three colors with respect to the under-exposure negative print administration are computed.

In Step 163, computation is executed to multiply the color-key corrections of the three colors obtained in Step 161 with variable constants so that exposure time correction factors are computed for three colors with respect to the under-exposure negative print.

In Step 164, the exposure time correction factors or the key-correction values as determined above are displayed on a liquid crystal display in accordance with the mode.

The completion of the processes for the normal, under and over exposures is detected in Step 165 and, in Step 166, a mode check is executed. In Step 167, a judgment is conducted as to whether the instant mode is a time mode. When the instant mode is the time mode, in Step 168, the exposure time correction factor data as determined above are read from the RAM 87 for each of the normal negative exposure time correction factor, over negative exposure time correction factor and the under negative exposure correction factor. When the instant mode is not the time mode, the color-key correction data and the density correction data determined as above are read from the normal negative exposure time key correction value, over negative exposure time key correction value and the under negative exposure time key correction value. These data are output from the RS-232C interface 89 in Step 170 and, in Step 171, the read data are printed by the thermal printer 81. The process then returns to the main routine.

Figure 19:
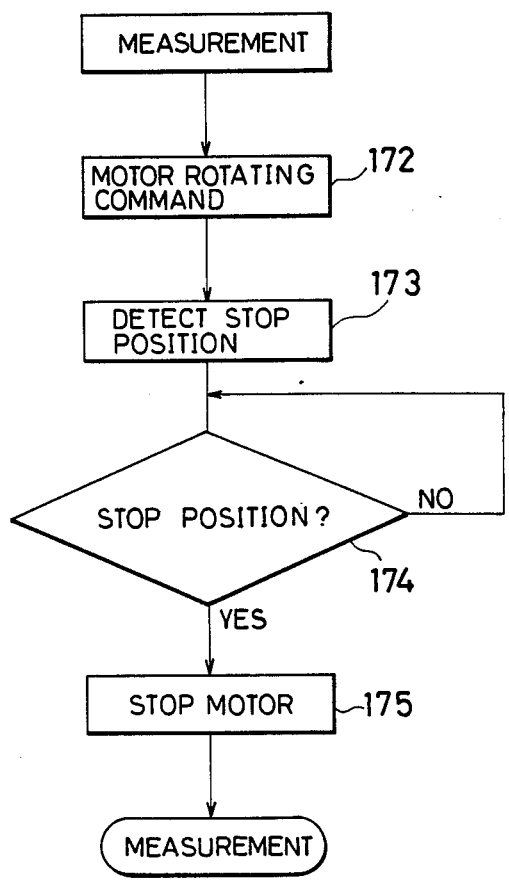

Although not shown in FIGS. 18A, 18B, 18C and 18D, the following steps are followed as shown in FIG. 19 between the processings for different colors: input of instructions for driving the motor (Step 172), detection of the stop positon (Step 173), judgment as to whether the instant position is the stopping position (Step 174), and processing and judgment for stopping the motor (Step 175).

The densitometer of this embodiment, therefore, is capable of storing the reference density values or the AIM density values in the respective channels of the RAM 87. This can be conducted by manual input through the keyboard or by reading of the reference densities. The differences between the stored reference densities and the measuring density values are converted into the correction values for the exposure time correction for the color printer (time values for red, green and blue), color keys for the exposure time correction (red, green and blue) and the key-correction values of the density, and are displayed and externally output.

The color printers have different color-key and density-key correction factors according to the type of the printers and the manufacturers. The color time correction factors and the density time correction factors, however, can be input even though they are varied.

The change-over of the output mode also enables the display and external output of the slope correction data (exposure time correction factors and color-key and density-key correction values for the red, green and blue colors) with respect to the normal exposure negative, over-exposure negative and under-exposure negative for the color printer.

As has been described, according to the densitometer of the present invention, it is possible to measure, with a single light-receiving element, all the densities such as transmission density of a color negative film, reflection density of a color print, transmission density of a color reversal film, transmission density of a monochromatic film, reflection density of monochromatic print. This appreciably facilitates the operation for measuring the reflection density and the transmission density. In addition, the number of the parts is reduced and the installation space also is saved, with the result that the cost is reduced as well as the size. Furthermore, the measuring conditions can be uniformalized to provide a higher precision. Furthermore, the difference between the measured density and the reference density is converted into the color-key correction value, density-key correction value and the exposure time correction factor which are displayed in the display and externally output through an interface. In addition, the invention offers a practical advantage that both the reflection density and the transmission density are measured with a single densitometer.

In this densitometer, the disk is rotated by the motor to select the desired filter so that both the reflection density and the transmission density are measurable by a single light-receiving element. The difference between the measured density and the reference density is converted into color-key correction value, density-key correction value and exposure time correction factor which are displayed on a display unit. This data can be externally output through an interface.

What is claimed is:

1. A densitometer for photography comprising:
    a disk on which are disposed at a predetermined circumferential spacing filters of three colors for measuring the transmission density of a negative film, filters of three colors for measuring the reflection density of a color print and for measuring the transmission density of a color reversal film, and a visual sensitivity filter for measuring the reflection density of a monochromatic print, a transmission density of a monochromatic film and a transmission density of a monochromatic reversal film;
    a lamp for enabling the measurement of the reflection densities;
    a lamp for enabling the measurement of the transmission densities;
    a light-receiving element;
    a motor for rotatingly driving said disk as to bring the seven filters into alignment with said light receiving element in a one-by-one fashion;
    a density measuring portion for measuring the density from the output of said light-receiving element;
    a density difference computing means for determining the difference between the measured density and a reference density stored in a memory of a computing processor;
    a color-key correction value computing means for computing a color-key correction value from said difference;
    a density-key correction value computing means for computing the density-key correction value from said difference;
    an exposure time correction factor computing means for computing the exposure time correction factor from said color-key correction value;
    a display means for displaying the computed color-key correction value, density-key correction value and the exposure-time correction factor; and
    an interface for externally outputting the data concerning these values and factor.

2. A densitometer for photography characterized in that:
    a reflection density measuring lamp, a transmission density measuring lamp and a single light-receiving element are disposed at predetermined positions;
    a tri-color filter for measuring the transmission density of a negative film, a tri-color filter for measuring the reflection density of a color print and for measuring the transmission density of a color reversal film, and a visibility filter for measuring the reflection density of a monochromatic print, a transmission density of a monochromatic film and a transmission density of a monochromatic reversal film, disposed on a disk at a predetermined spacing in the circumferential direction;
    said disk is rotated by a motor so as to bring the seven filters into alignment with the light-receiving element in a one-by-one fashion; and
    that an aperture is formed in a transparent guide plate contacting a measuring object, said aperture being intended for limiting the light which is applied by said reflection density measuring lamp to said measuring object or the light which is applied by said transmission density measuring lamp to the filter opposing to said light-receiving element through said measuring object.

3. A densitometer for photography according to claim 2, further comprising: stop position detection holes formed in said disk in such a manner as to correspond to said seven filters, and a sensor capable of sensing said detection holes.

* * * * *